United States Patent [19]
Bonnell et al.

[11] Patent Number: 4,766,154
[45] Date of Patent: Aug. 23, 1988

[54] LIQUID PHASE METHANOL REACTOR STAGING PROCESS FOR THE PRODUCTION OF METHANOL

[75] Inventors: Leo W. Bonnell; Alan T. Perka, both of Macungie; George W. Roberts, Emmaus, all of Pa.

[73] Assignee: Air Products and Chemicals, Inc., Allentown, Pa.

[21] Appl. No.: 11,647

[22] Filed: Feb. 6, 1987

[51] Int. Cl.$^4$ ............................................. C07C 27/06
[52] U.S. Cl. ................................. 518/700; 518/706
[58] Field of Search ................................ 518/700, 706

[56] References Cited

U.S. PATENT DOCUMENTS

| | | | |
|---|---|---|---|
| 1,959,219 | 5/1934 | Reed | 260/116 |
| 3,888,896 | 6/1975 | Epino et al. | 260/449.5 |
| 4,031,123 | 6/1977 | Epino et al. | 260/449.5 |
| 4,235,799 | 11/1980 | Wentworth et al. | 260/449.5 |
| 4,346,179 | 8/1982 | Sugier et al. | 518/707 |
| 4,423,250 | 12/1983 | Fachinetti | 518/700 X |
| 4,477,594 | 10/1984 | Greene et al. | 518/700 |
| 4,567,204 | 1/1986 | Mednick et al. | 518/700 |
| 4,628,066 | 12/1986 | Bonnell et al. | 518/700 |

FOREIGN PATENT DOCUMENTS 1157053 11/1983 Canada .............................. 260/638

Primary Examiner—Howard T. Mars
Attorney, Agent, or Firm—Willard Jones, II; James C. Simmons; William F. Marsh

[57] ABSTRACT

The present invention is a process for the production of methanol from a syngas feed containing carbon monoxide, carbon dioxide and hydrogen. Basically, the process is the combination of two liquid phase methanol reactors into a staging process, such that each reactor is operated to favor a particular reaction mechanism. In the first reactor, the operation is controlled to favor the hydrogenation of carbon monoxide, and in the second reactor, the operation is controlled so as to favor the hydrogenation of carbon dioxide. This staging process results in substantial increases in methanol yield.

3 Claims, 1 Drawing Sheet

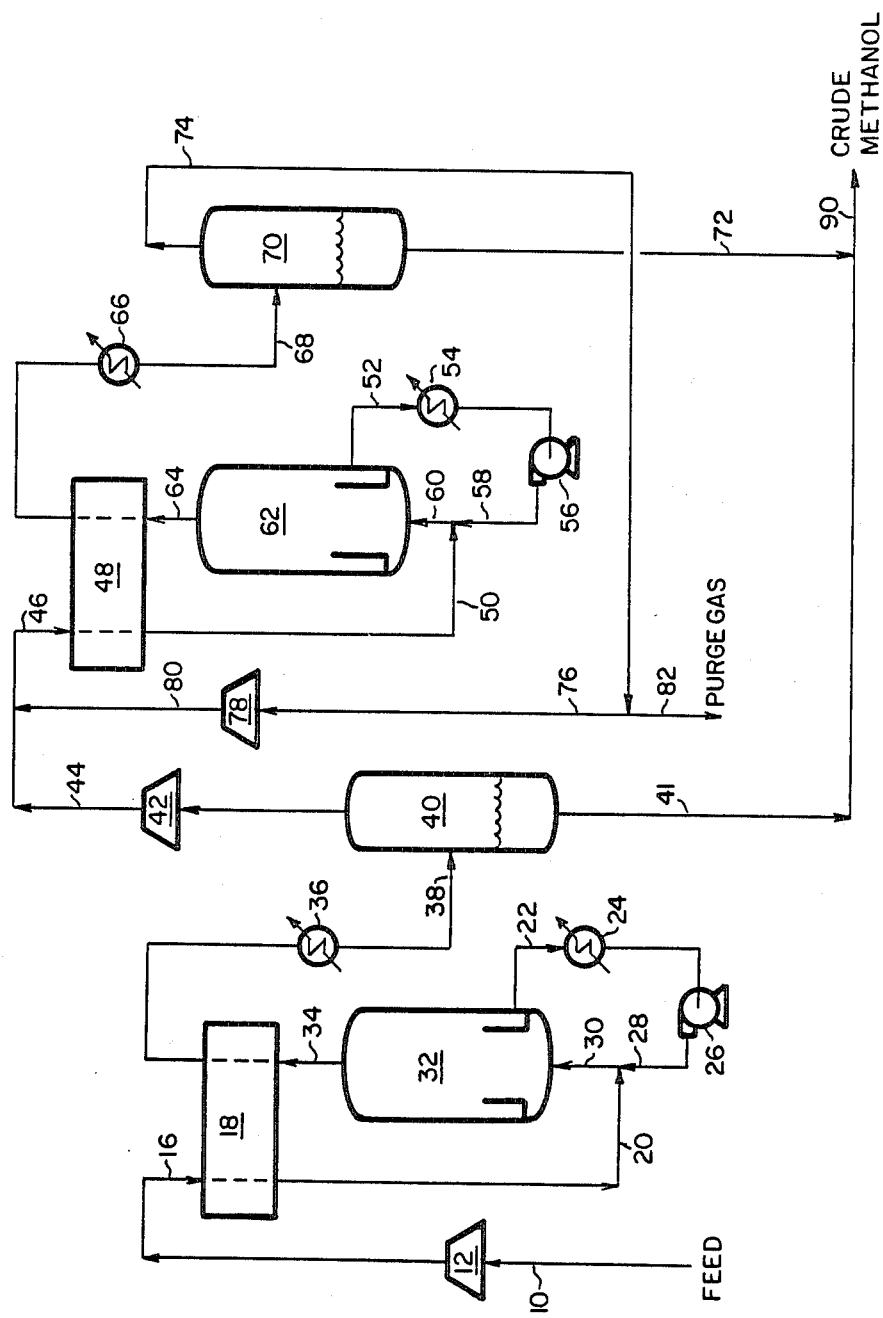

LIQUID PHASE METHANOL REACTOR STAGING PROCESS FOR THE PRODUCTION OF METHANOL

TECHNICAL FIELD OF THE INVENTION

The present invention relates to the production of methanol from a syngas feed comprising carbon monoxide, carbon dioxide and hydrogen.

BACKGROUND OF THE INVENTION

Various methods have been developed for the production of methanol from gas mixtures containing carbon oxides and hydrogen, among these are:

U.S. Pat. No. 4,628,066 discloses a process for increasing the capacity of a gas phase synthesis loop for the productio of methanol from a syngas feed. The syngas feed is initially passed to a liquid phase methanol reactor to convert a portion of the syngas to methanol or methanol and higher aliphatic alcohols. The mixture is subsequently cooled to condense and recover the methanol and/or higher alcohols. The unreacted syngas is passed to a gas phase synthesis loop for further conversion and recovery of methanol.

U.S. Pat. No. 4,567,204 discloses a process for the production of methanol in a liquid phase methanol reactor by entraining a methanol-forming catalyst in an inert liquid and contacting the entrained catalyst with a synthesis gas comprising carbon monoxide and hydrogen.

U.S. Pat. No. 4,346,179 discloses a process for producing methanol and its higher homologs from a synthesis gas containing essentially carbon dioxide, carbon monoxide and hydrogen. A synthesis gas is treated in a first catalytic reaction zone at 230°–350° C. The effluent from the first catalytic reaction zone is cooled and condensed and a gas fraction is separated from the liquid condensate. The gas fraction is subsequently treated at 240°–300° C. in a second catalytic reaction zone to produce a liquid methanol fraction. The liquid methanol fraction is subsequently admixed with the liquid condensate to form a gasoline constituent product.

U.S. Pat. No. 4,235,799 discloses a process for producing methanol by passing a mixture of hydrogen and one or more carbon oxides into contact with at least two beds of catalyst arranged in series. The catalyst beds are operated at increasing temperature levels in the direction of flow of the mixture. The mixture is subsequently cooled by indirect heat exchange and passed into contact with at least one further bed of catalyst.

U.S. Pat. No. 4,031,123 discloses a similar method for preparing methanol with the improvement that paraffinics and cycloparaffinics are used as the inert hydrocarbon liquid in which the catalyst bed is in contact.

U.S. Pat. No. 3,888,896 discloses a process for producing methanol from carbon monoxide and hydrogen by saturating an inert organic liquid medium, such as pseudocumene, with carbon monoxide and hydrogen and contacting the saturated liquid medium with a methanol-forming catalyst such as those containing zinc and chromium.

U.S. Pat. No. 1,868,096 discloses a process for producing methanol by passing a reaction gas mixture under the requisite conditions of temperature and pressure initially over one or more catalyst masses composed of zinc oxide or zinc oxide and chromium oxide and subsequently passing said mixture over one or more methanol catalysts sensitive to sulfur poisoning such as catalysts comprising copper, manganese or compounds of copper or manganese. The reaction gases are passed successively through a number of reactor vessels arranged in series as an open system.

Canadian Pat. No. 1,157,053 discloses a liquid phase methanol synthesis process wherein methanol is produced by contacting a synthesis gas comprising hydrogen and carbon monoxide with a catalyst in the presence of an inert liquid. The catalyst in contact with the inert liquid is in the form of particles of a size less than about 125 microns.

BRIEF SUMMARY OF THE INVENTION

The present invention is an improvement to a staged process for the production of methanol from a syngas feed stream containing carbon monoxide, carbon dioxide and hydrogen. The improvement comprises utilizing two liquid phase methanol reactors such that the syngas feed stream is passed to the first liquid phase methanol reactor to convert a portion of the syngas to methanol and thereby form a methanol-containing first reactor effluent. This first reactor effluent is cooled to condense out the methanol and thus produce a first methanol stream and an unreacted syngas stream. The unreacted syngas stream is then passed to the second liquid phase methanol reactor to convert at least a portion of the unreacted syngas stream to methanol, thereby forming a methanol-containing second reactor effluent. This second reactor effluent is cooled to condense out the methanol and thus produce a second methanol stream and a second unreacted gas stream. The first and second methanol streams are recovered as product. As a preferred option, the second unreacted syngas stream is recycled to the second liquid phase reactor. The reaction conditions in the first reactor favor the conversion of CO over $CO_2$ relative to the second reactor and conditions in the second reactor favor the conversion of $CO_2$ over CO relative to the first reactor.

BRIEF DESCRIPTION OF THE DRAWINGS

The single FIGURE is a schematic flow diagram of a preferred embodiment of the present invention.

DETAILED DESCRIPTION OF THE INVENTION

There are two primary reaction mechanisms for the production of methanol by hydrogenation of a carbon monoxide and carbon dioxide containing gas mixture, these are:

$$CO + 2H_2 \rightleftharpoons CH_3OH \tag{1}$$

$$CO_2 + 3H_2 \rightleftharpoons CH_3OH + H_2O \tag{2}$$

with reaction (2) really being a series of reactions as follows:

$$CO_2 + H_2 \rightleftharpoons CO + H_2O \tag{3}$$

followed by:

$$CO + 2H_2 \rightleftharpoons CH_3OH \tag{4}$$

For a $CO/CO_2/H_2$ feed gas, the reaction preference will strongly be in favor of reaction (1), and it is not until the concentration of CO with respect to $CO_2$ is sufficiently low that the thermodynamics and kinetics will favor reaction (2), in reality reaction (3). Based on this fact, the ideal process for the production of methanol by hydrogenating a $CO/CO_2$ gas feed would be to react the $CO/CO_2/H_2$ feed gas in a first reactor wherein the operating conditions are preferentially set to favor reaction (1) thereby reducing the concentratio of CO with respect to $CO_2$ and setting up the appropriate kinetic and thermodynamic conditions for reaction (3), and further reacting any unconverted feed gas in a second reactor wherein the operating conditions are preferentially set to favor reaction (3), thus resulting in an increased yield of methanol.

To accomplish the above process the absolute conversion of CO must be high in the first reactor, however, reaction (1) is highly exothermic. Therefore, if the heat from the reaction is not removed, the reaction temperature rises, and as reaction temperature rises, the equilibrium of reaction (1) shifts and eventually limits further conversion of CO and $H_2$ to methanol. To prevent a shift in the equilibrium of reaction (1), the reaction temperature must be kept nearly isothermal. Thus, the process requires two things, high absolute conversion, i.e. high methanol concentration in the reactor effluent, and near isothermal operation.

If a conventional gas phase reactor is used as the first reactor in the above process, a near isothermal reaction temperature would be accomplished by recycling unreacted material back to the reactor and keeping the per pass methanol-make (concentration) low. Dilution of the fresh feed inherently negates the possibility of preferentially reacting the CO while the CO concentration is high. That is, the recycle gas not only dilutes the CO (as well as the $CO_2$), but also lowers the $CO/CO_2$ ratio of the synthesis gas; thus selective reaction of the CO is impaired. The result is a process involving parallel CO and $CO_2$ reactions, with the potential benefits of reaction segregation neutralized. This is quite different from the result achieved in the process of the invention. Furthermore, the maximum methanol-make that can be expected utilizing a convential gas phase reactor is equivalent to approximately 4–6% methanol concentration in the reactor effluent. Therefore, a conventional gas phase reactor is not applicable for effective use as the first stage in the above process.

On the other hand, when a liquid phase methanol (LPMeOH) reactor is utilized the reactor temperature can be kept basically isothermal and high methanol concentrations can be accomplished, i.e. in excess of 10%. This high methanol-make is accomplished primarily through the conversion of concentrated CO, which is the precise goal for operation. Therefore, once the CO concentration has been lowered (relative to $CO_2$ concentration) the reaction conditions can be modified to favor reaction (3), the result being a notable increase in per pass production of methanol. It is precisely this ability to obtain high conversion of CO in the first liquid phase methanol reactor and therefore gain the ability to perform the reverse shift reaction (3), that is the unexpected result, i.e. it is the only reactor type that can accomplish the process.

To better illustrate the process of the present invention, the single FIGURE of the drawing is offered. With reference to that FIGURE, a synthesis gas feed stream, which is fed to the process via line 10, is compressed in compressor 12. This compressed feed stream is then heated by heat exchange in heat exchanger 18 against cooling effluent from reactor 32. This heated compressed feed stream is then united with recycle liquid in stream 28 from the bottom of first liquid phase methanol reactor 32 to form combined feed stream 30. A liquid recycle stream, in line 22, is removed from the bottom of reactor 32, cooled in heat exchanger 24, pumped to pressure with pump 26, prior to being united via line 28 with fresh feed stream 20 and fed to reactor 32 in line 30. The reactor effluent is removed via line 34 from reactor 32 and is cooled in two steps, first in heat exchanger 18 against warming fresh feed and then in heat exchanger 36. The cooled first reactor effluent, now in line 38, is then separated in separator 40. The bottoms liquid from separator 40 is removed from the process via line 41 as a crude methanol product.

The first reactor vapor phase from separator 40 is compressed in compressor 42. This compressed vapor phase stream is combined with second reactor vapor phase stream 80 to form stream 46. This combined stream 46 is warmed in heat exchanger 48 against cooling effluent from reactor 62. The heated stream in line 50 is then united with recycle liquid in stream 58 from the bottom of second liquid phase methanol reactor 62 to form combined feed stream 60. A liquid recycle stream, in line 52, is removed from the bottom of reactor 62, cooled in heat exchanger 54, pumped to pressure with pump 56, prior to being united via line 58 with fresh feed stream 50 and fed to reactor 62 in line 60. The reactor effluent is removed via line 64 from reactor 62 and is cooled in two steps, first in heat exchanger 48 against warming fresh feed and then in heat exchanger 66. The cooled second reactor effluent, now in line 68, is then separated in separator 70. The bottoms liquid from separator 70 is removed from the process via line 72 as a crude methanol product. This crude methanol product in line 72 can be let down in pressure and united with the crude methanol product in line 41 to form a combined methanol product which is removed from the process in line 90.

The second reactor vapor phase from separator 70 is removed via line 74. A small purge is removed from line 74 via line 82; the purpose of the purge is to control the concentration of nonreactant contaminants in the recycle stream. The remaining portion, now in line 76, is compressed in compressor 78 and combined with first reactor vapor phase feed in line 44.

In the FIGURE and the above discussion, the first reaction zone is shown as consisting of a single liquid-phase methanol reactor, reactor 32, however, one skilled in the art would recognize that if necessary, because of certain constraints among such being a maximum reactor vessel diameter, that this single reactor could be replaced by two or more reactors either in series or in parallel. Similarly, the same is true of the second reactor, reactor 62.

In order to show the efficacy of the present invention and to provide a comparison of the process of the present invention with the prior art processes, the following example is offered.

EXAMPLE

A computer simulation was run of the process of the present invention as depicted in the single FIGURE of the drawing utilizing a copper-zinc commercial methanol catalyst in a powder form. A material balance for the process producing about 2,740 tons per day of methanol is shown in Table I. In the example, fresh feed in line 10 is compressed in compressor 12, heated in heat exchanger 18, and fed to first liquid phase methanol reactor 32, which operates at 1000 psia (6984 kPa) and 482° F. (250° C.). In reactor 32, 59 mol % of the carbon monoxide and 14 mol % of the carbon dioxide are converted to methanol. The methanol concentration in the reactor 32 effluent, line 34, is about 12 mol %. The reactor 32 effluent, line 34, is cooled to condense the methanol product, which is facilitated by the high concentration, and any water. After separation the compressed unreacted gas in line 44 is combined with recycle gas in line 80, and fed via line 50 to second liquid phase methanol reactor 62. Second reactor 62 operates at 1500 psia (10,476 kPa) and 482° F. (250° C.) and converts 72 mol % of the carbon monoxide and 64 mol % of the carbon dioxide to methanol. The methanol concentration in reactor 62 effluent is about 5 mol %. Reactor 62 effluent, in line 64, is cooled in heat exchangers 48 and 66 to condense the methanol product.

The advantage of the present invention is that a greater proportion of the carbon monoxide is converted in reactor 32, thus, better advantage is taken of the liquid phase methanol reactor's heat removal ability. Taking advantage of the liquid phase methanol reactor's heat removal ability results in a better separation of the reaction mechanisms.

Referring to the example, the unreacted gas from first reactor 32 is compressed in compressor 42 to 1500 psia (10476 kPa). Since a high conversion is accomplished in first reactor 32, it it feasible to compress the lower gas flow to a higher pressure. This higher pressure favors the equilibrium and kinetics of both CO and $CO_2$ reactions, but the $CO_2$ reaction is favored preferentially.

The separation of reactions is further demonstrated

TABLE I
MATERIAL BALANCE
LIQUID PHASE METHANOL REACTOR STAGED PROCESS

| STREAM NUMBER: | 10 | 16 | 20 | 34 | 38 | 44 | 46 | 50 |
|---|---|---|---|---|---|---|---|---|
| PRESSURE: PSIA | 240 | 1000 | 990 | 980 | 960 | 1500 | 1500 | 1490 |
| KPA | 1654 | 6984 | 6825 | 6756 | 6618 | 10341 | 10341 | 10272 |
| TEMPERATURE: °F. | 100 | 154 | 260 | 482 | 105 | 215 | 136 | 348 |
| °C. | 38 | 68 | 127 | 250 | 41 | 102 | 57 | 176 |
| TOTAL FLOW: LB/HR | 321,122 | 321,122 | 321,122 | 321,122 | 321,122 | 210,227 | 563,197 | 563,197 |
| COMPOSITION: MOL % | | | | | | | | |
| HYDROGEN | 73.36 | 73.36 | 73.36 | 65.43 | 65.43 | 75.68 | 81.38 | 81.38 |
| CARBON MONOXIDE | 14.92 | 14.92 | 14.92 | 7.64 | 7.64 | 8.83 | 2.86 | 2.86 |
| CARBON DIOXIDE | 7.81 | 7.81 | 7.81 | 8.36 | 8.36 | 9.21 | 3.27 | 3.27 |
| METHANE | 3.71 | 3.71 | 3.71 | 4.62 | 4.62 | 5.31 | 11.40 | 11.40 |
| NITROGEN | 0.19 | 0.19 | 0.19 | 0.24 | 0.24 | 0.27 | 0.60 | 0.60 |
| WATER | 0.01 | 0.01 | 0.01 | 1.40 | 1.40 | 0.03 | 0.05 | 0.05 |
| METHANOL | 0.00 | 0.00 | 0.00 | 12.28 | 12.28 | 0.67 | 0.44 | 0.44 |
| ETHANOL | 0.00 | 0.00 | 0.00 | 0.01 | 0.01 | 0.00 | 0.00 | 0.00 |
| METHYL FORMATE | 0.00 | 0.00 | 0.00 | 0.02 | 0.02 | 0.00 | 0.00 | 0.00 |
| STREAM NUMBER: | 64 | 74 | 76 | 80 | 82 | 41 | 72 | 90 |
| PRESSURE: PSIA | 1480 | 1460 | 1460 | 1500 | 1460 | 950 | 1460 | 950 |
| KPA | 10203 | 10065 | 10065 | 10341 | 10065 | 6549 | 10065 | 6549 |
| TEMPERATURE: °F. | 482 | 105 | 105 | 110 | 105 | 105 | 105 | 105 |
| °C. | 250 | 41 | 41 | 43 | 41 | 41 | 41 | 41 |
| TOTAL FLOW: LB/HR | 563,197 | 397,643 | 352,970 | 352,970 | 44,673 | 110,895 | 165,554 | 276,449 |
| COMPOSITION: MOL % | | | | | | | | |
| HYDROGEN | 77.42 | 83.26 | 83.26 | 83.26 | 83.26 | 0.27 | 0.38 | 0.34 |
| CARBON MONOXIDE | 0.86 | 0.92 | 0.92 | 0.92 | 0.92 | 0.11 | 0.01 | 0.05 |
| CARBON DIOXIDE | 1.29 | 1.35 | 1.35 | 1.35 | 1.35 | 2.95 | 0.53 | 1.43 |
| METHANE | 12.43 | 13.34 | 13.34 | 13.34 | 13.34 | 0.23 | 0.46 | 0.37 |
| NITROGEN | 0.65 | 0.70 | 0.70 | 0.70 | 0.70 | 0.00 | 0.00 | 0.00 |
| WATER | 2.34 | 0.05 | 0.05 | 0.05 | 0.05 | 10.15 | 32.42 | 24.12 |
| METHANOL | 5.01 | 0.37 | 0.37 | 0.37 | 0.37 | 86.11 | 66.07 | 73.54 |
| ETHANOL | 0.00 | 0.00 | 0.00 | 0.00 | 0.00 | 0.09 | 0.07 | 0.08 |
| METHYL FORMATE | 0.00 | 0.01 | 0.01 | 0.01 | 0.01 | 0.08 | 0.06 | 0.07 |

Note, that in the example the fresh feed composition in line 10 contains a $CO/CO_2$ molar ratio of about 2:1, a composition typical of that from a steam methane reformer. Because of the high ratio of $CO/CO_2$, it is clear that very high CO depletion will be necessary if the subsequent conversion of $CO_2$ is to be favored. This conversion of CO to methanol takes place primarily in reactor 32 via the following reaction:

$$CO + H_2 \rightarrow CH_3OH \qquad \Delta H = -38,995 \text{ BTU/lb-mol}$$

After product separation, conditions are favorable for the more difficult conversion of $CO_2$ to methanol in the second reactor via the following reaction:

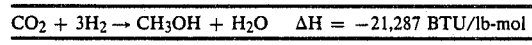

$$CO_2 + 3H_2 \rightarrow CH_3OH + H_2O \qquad \Delta H = -21,287 \text{ BTU/lb-mol}$$

with reference to Table II. Here one sees that 89% of the methanol produced in reactor 32 comes from CO and 11% comes from $CO_2$; in reactor 62 only 50% of the methanol comes from CO, with the balance coming from $CO_2$ conversion. For the sake of comparison, Table II also shows the corresponding data for other state of the art processes with the same nominal production basis. In Table II, the first set of columns under the heading "Staged LPMeOH" corresponds to the process of the present invention, the second set of columns under the heading "Staged Combination" corresponds to the process described in U.S. Pat. No. 4,628,066, the third set of columns under the heading "Staged Gas Phase" corresponds to a process similar to the one described in U.S. Pat. No. 4,346,179, and the final column under the heading "Conventional Gas Phase" corresponds to a conventional gas phase process with a single adiabatic, quench-type reactor with recycle.

TABLE II

COMPARISON OF TWO-STAGE LPMEOH PROCESS TO GAS-PHASE AND LIQUID-PHASE/GAS-PHASE PROCESSES

| Reactor Type & Number | STAGED LPMeOH | | STAGED COMBINATION | | STAGED GAS-PHASE | | CONVENTIONAL GAS PHASE |
|---|---|---|---|---|---|---|---|
| | LP-01 | LP-02 | LP-01 | GP-02 | GP-01 | GP-02 | GP-01 |
| % CO in Reactor Feed | 14.9 | 2.8* | 14.9 | 2.2* | 9.8° | 1.7° | 3.7* |
| % $CO_2$ in Reactor Feed | 7.8 | 3.3* | 7.8 | 2.2* | 7.5* | 1.5° | 2.5° |
| Feed $CO/CO_2$ | 1.9 | 0.9 | 1.9 | 1.0 | 1.30 | 1.13 | 1.5 |
| % CO Conversion | 59 | 72 | 59 | 52 | 39 | 51 | 61 |
| % $CO_2$ Conversion | 14 | 64 | 14 | 54 | 16 | 61 | 47 |
| % of MeOH from CO | 89 | 50 | 89 | 49 | 76 | 49 | 66 |
| % of MeOH from $CO_2$ | 11 | 50 | 11 | 51 | 24 | 51 | 34 |
| % MeOH in Reactor Effluent | 12 | 5 | 12 | 3 | 6.0 | 2.2 | 4 |
| Reaction Exotherm per lbmole of Feed Gas, BTU/lb-mole | 3,672 | 1,252 | 3,672 | 709 | 1,741 | 531 | 1,148 |
| Reactor Methanol Production, TPD | 1,190 | 1,548 | 1,190 | 1,548 | 1,795 | 943 | 2,747 |
| Total Methanol Production, TPD (w/EtoH credit) | 2,738 | | 2,738 | | 2,738 | | 2,747 |
| Reactor throughput,** lb-mol/hr | 32,950 | 93,420 | 32,950 | 164,486 | 95,563 | 132,754 | 209,000 |
| Recycle Ratio | — | 3.1 | — | 6.2 | 1.90 | 6.73 | 5.3 |
| Per Pass Methanol-Make Ratio $\times 10^{2}$*** | 3.61 | 1.66 | 3.61 | 0.94 | 1.88 | 0.71 | 1.31 |

*Diluted by recycle gas.
**At reactor inlet.
***Reactor methanol production/reactor throughput Several parameters are presented in Table II to describe the process performance. One such factor and a confusing one at that is percent CO or $CO_2$ conversion. percent conversion is useful and meaningful in describing the relative consumption of reactants, however, it is not a meaningful measure of the reactor's heat load, or more importantly, the heat load per unit of gas throughput. The reason it is not a meaningful measure of heat load is because the exotherm in the reactor, defined in Table II as the amount of heat released per unit of feed gas, is proportional to the amount of product produced per unit throughput, which in turn depends on the reactant concentrations. If the reactants are very dilute, as is the case with gas phase reactors, then even a high percent CO conversion will produce relatively little methanol per unit throughput, and the corresponding exotherm is small.

Another parameter which describes process performance is the percent methanol from CO and $CO_2$. This parameter measures the percentage of the methanol produced in the reactor from either CO or $CO_2$ as the starting material.

Two meaningful parameters for describing the reactor's heat load intensity are the percent methanol concentration in the reactor effluent and the exotherm per unit (e.g. lb-mol) of feed. These parameters are approximately proportional to one another and both provide a measure of how "concentrated" the exotherm is, i.e. how much of the feed is actually reacting and releasing energy.

The last meaningful parameter is reactor throughput, which directly determines reactor size.

As can be seen from the data in Table II, when the first stage is a liquid phase methanol reactor, no recycle is required; the exit methanol concentration is about 12%, and because of the once-through operation, the reactor throughput is low. In other words, the amount of methanol produced per unit of throughput is high. If the first stage is a gas phase reactor, recycle is required to dilute the reactants; this lowers the exotherm per lb-mol of feed. In the staged process utilizing two gas phase reactors, the outlet methanol was set as high as feasible at 6%. Because of the recycle necessary to limit the outlet methanol concentration at 6%, the reactor throughput that is required is nearly three times that for the once through liquid phase methanol reactor unit. The segregation of reactions is also poorer when a gas phase reactor is used in the first stage. For the once through liquid phase methanol reactor, 89% of the methanol comes from CO; for the first stage in the staged gas process, 76% of the methanol comes from CO, and for the single gas phase reactor, the fraction of methanol from CO is only 66%. This shows that the segregation of reactions becomes poorer as recycle is increased.

As for the second stage for both the liquid phase methanol reactor and gas phase reactor cases, looking only at the percent methanol from CO and $CO_2$, there appears to be little difference in the segregation of the reactions in the second stage. This result is forced here by an implicit specification of high overall carbon conversion, from both CO and $CO_2$, to methanol product. It should be noted, however, that the liquid phase methanol reactor process second stage requires much less throughput to accomplish the same or greater methanol production. This supports the claim that after CO concentration has been lowered relative to $CO_2$ in the first stage, the reaction conditions have been successfully modified to favor the $CO_2$ synthesis reaction, the result being an increase in the per pass production of methanol in the second liquid phase methanol reactor. As can be seen from Table II, the per pass methanol-make ratio ($\times 10^2$) is much higher for the liquid phase reactor as the second stage than the gas phase reactor, 1.66 for liquid phase of 0.94 for gas phase.

The segregation of reactions is even more apparent when the processes are compared on a fixed reactor throughput, rather than a fixed production, basis. Such a comparison is shown in Table III, which contains results for the second stages of the "Staged LPMeOH" and "Staged Combination" processes at constant throughput, i.e. identical recycle ration. The first stage for both processes is a once through LPMeOH reactor identical to that in Table II.

TABLE III

COMPARISON OF SECOND-STAGE GAS-PHASE AND
LIQUID-PHASE REACTORS AT A FIXED THROUGHPUT
OF 68,536 lb-mol/hr (Recycle Ratio = 2.0)

|  | LP-02 | GP-02 | % Relative Change from Gas to Liquid |
|---|---|---|---|
| % CO Conversion | 72 | 53 | +35.8 |
| % $CO_2$ Conversion | 57 | 35 | +62.9 |
| % of MeOH from CO | 51 | 54 | −5.6 |
| % of MeOH from $CO_2$ | 49 | 46 | +6.5 |
| Reactor MeOH Production: TPD | 1,485 | 1,281 | +15.5 |
| MeOH via CO: TPD | 756 | 686 | +10.2 |
| MeOH via $CO_2$: TPD | 729 | 595 | +22.5 |
| CO Per Pass MeOH - Make Ratio (MeOH via CO/CO throughput) | 0.29 | 0.21 | +38.1 |
| $CO_2$ per Pass MeOH - Make Ratio (MeOH via $CO_2/CO_2$ throughput) | 0.23 | 0.14 | +64.3 |

Referring to Table III, in the LPMeOH second stage the percentage of methanol from CO is 5.6% lower relative to the gas-phase reactor, and the percentage of methanol from $CO_2$ is 6.5% higher. The liquid phase methanol reactor production is 15.5% greater than that for the gas-phase reactor, and the increase in methanol production via $CO_2$ hydrogenation is twice the increase in methanol production via CO hydrogenation. The most dramatic evidence of the increased productivity and segregation of reactions is seen in the CO and $CO_2$ per pass methanol make ratios, as defined in Table III. The increase in the $CO_2$ per pass methanol make ratio for the LPMeOH reactor is over 64% greater than that for a gas-phase reactor with the same throughput.

From an analysis of the data presented in Tables II and III, it is evident that the staged liquid phase methanol reactor process of the present invention is a preferred and better process to produce methanol. Utilizing the process of the present invention, the same amount of production can be attained as other conventional processes yet achieve a significant reduction in reactor throughputs and thus reactor sizes; a more efficient handling of the reaction exotherm and a higher percentage of methanol in the reactor effluent are accomplished, a result of being able to operate at high conversions yet minimize the need for a diluent.

The present invention has been described with reference to a preferred embodiment thereof. However, this embodiment should not be considered a limitation on the scope of the invention, which scope should be ascertained by the following claims.

We claim:

1. In a staged process for the production of methanol from a syngas feed stream containing carbon monoxide, carbon dioxide and hydrogen, the improvement comprising:

(a) passing the syngas feed stream to a first liquid phase methanol reactor to convert a portion of the syngas to methanol and thereby form a methanol-containing first reactor effluent;

(b) cooling the methanol-containing first reactor effluent to condense the methanol and thereby produce a first methanol stream and a first reactor unreacted syngas stream;

(c) passing the first reactor unreacted syngas stream to a second liquid phase methanol reactor to convert at least a portion of the first reactor unreacted syngas stream to methanol and thereby form a methanol-containing second reactor effluent;

(d) cooling the methanol-containing second reactor effluent; condense the methanol and thereby produce a second methanol stream and a second unreacted gas stream; and (e) recovering the first and second methanol streams as product;

wherein the reaction conditions in said first reactor are controlled to favor the conversion of CO to methanol over $CO_2$ to methanol relative to said second reactor and the reaction conditions of said second reactor are controlled to favor the conversion of $CO_2$ to methanol over CO to methanol relative to said first reactor.

2. The process of claim 1 wherein the improvement further comprises recycling at least a portion of the second unreacted syngas stream to the second liquid phase reactor.

3. The process of claim 1 wherein said second reactor is operated at a higher pressure than said first reactor.

* * * * *